US008181650B2

(12) United States Patent
Nelson et al.

(10) Patent No.: US 8,181,650 B2
(45) Date of Patent: May 22, 2012

(54) MULTITASK MEDICAL TREATMENT RESPIRATORY APPARATUS

(76) Inventors: Robert Fayette Andrew Nelson, Rosamond, CA (US); Gary Dalhquist, Running Springs, CA (US); John Garcia, Hacienda Heights, CA (US)

( * ) Notice: Subject to any disclaimer, the term of this patent is extended or adjusted under 35 U.S.C. 154(b) by 1643 days.

(21) Appl. No.: 10/876,427

(22) Filed: Jun. 24, 2004

(65) Prior Publication Data

US 2005/0028811 A1      Feb. 10, 2005

Related U.S. Application Data

(63) Continuation-in-part of application No. 10/439,612, filed on May 15, 2003, now abandoned.

(51) Int. Cl.
*A62B 7/10* (2006.01)
*A62B 23/02* (2006.01)
*A62B 7/04* (2006.01)
*A61M 15/00* (2006.01)
*A61M 16/10* (2006.01)
*F15C 1/08* (2006.01)
*F16K 31/26* (2006.01)

(52) U.S. Cl. ......... 128/205.17; 128/203.12; 128/204.24; 128/204.28

(58) Field of Classification Search ............. 128/202.28, 128/202.29, 203.11, 203.12, 205.15, 203.28, 128/206.17, 206.24, 203.26, 201.22, 201.23, 128/201.24, 205.17, 204.24, 204.25, 204.26, 128/204.28

See application file for complete search history.

(56) References Cited

U.S. PATENT DOCUMENTS

| | | | | |
|---|---|---|---|---|
| 3,490,452 A * | 1/1970 | Greenfield | ............... | 128/200.23 |
| 4,029,092 A * | 6/1977 | Morgan | ................... | 128/201.11 |
| 4,823,784 A * | 4/1989 | Bordoni et al. | ......... | 128/200.14 |
| 5,586,551 A * | 12/1996 | Hilliard | ..................... | 128/203.29 |
| 6,102,034 A * | 8/2000 | Buhlmann | .............. | 128/201.29 |
| 6,539,939 B2 * | 4/2003 | Rubin | ...................... | 128/203.15 |
| 6,857,428 B2 * | 2/2005 | Thornton | ................. | 128/206.21 |
| 6,860,268 B2 * | 3/2005 | Bohn et al. | .............. | 128/206.21 |

* cited by examiner

*Primary Examiner* — Gary Jackson
*Assistant Examiner* — Michael Mendoza
(74) *Attorney, Agent, or Firm* — Dennis W. Beech

(57) ABSTRACT

The multitask medical treatment respiratory apparatus may have a mask defining a chamber wherein the mask may have a first port, a second port and a venting valve. A reservoir bag having a first opening may be in communication with the first port or there may be a venturi device may be in communication with a second opening of the reservoir bag. One or more gas sources may be in communication with the venturi device. A medicant device may be mounted in the second port wherein the medicant device having a mouthpiece that may be inserted and retracted relative to the mask chamber and a patients mouth. The medicant device having a medicant chamber formed therein.

45 Claims, 5 Drawing Sheets

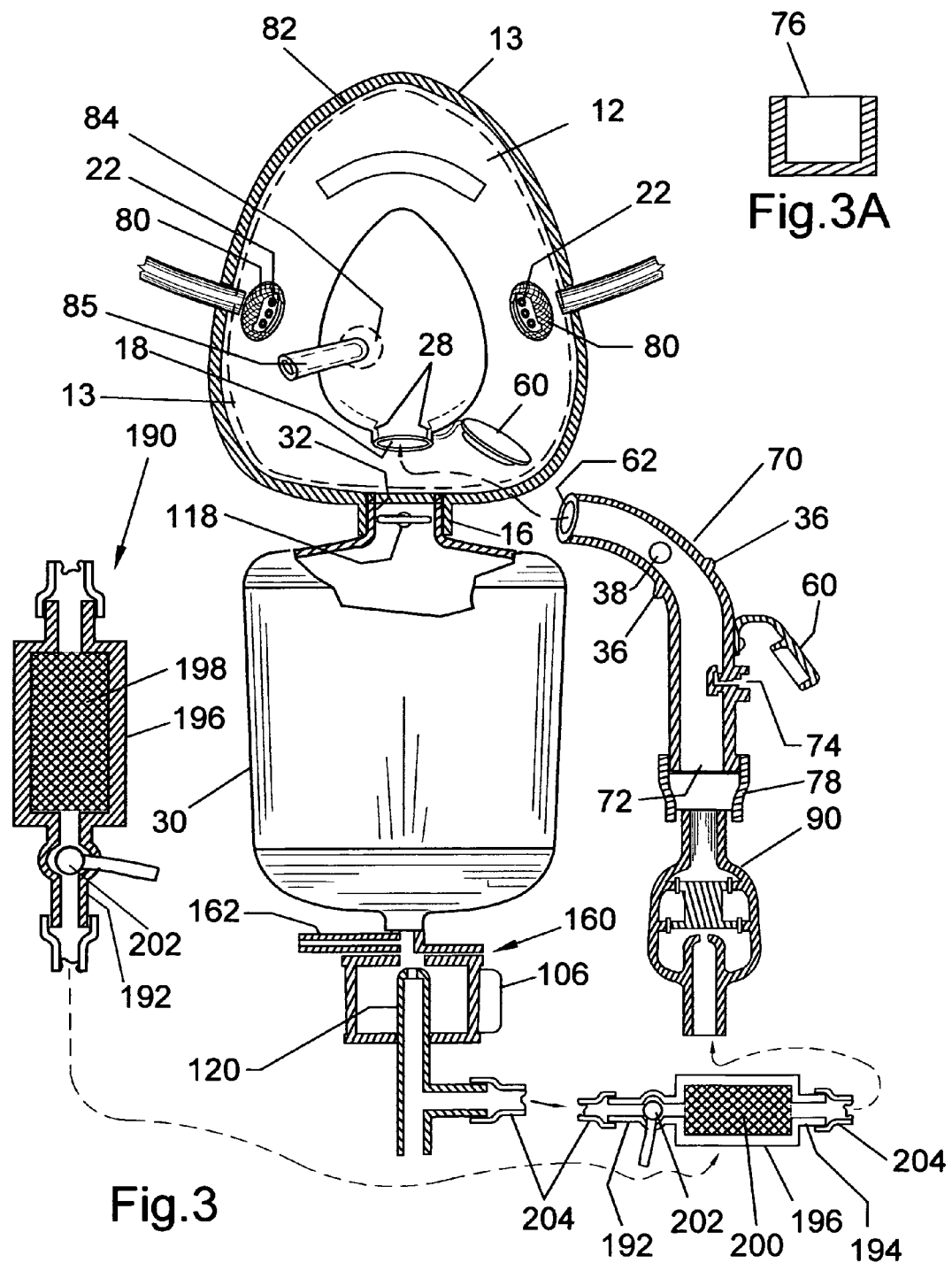

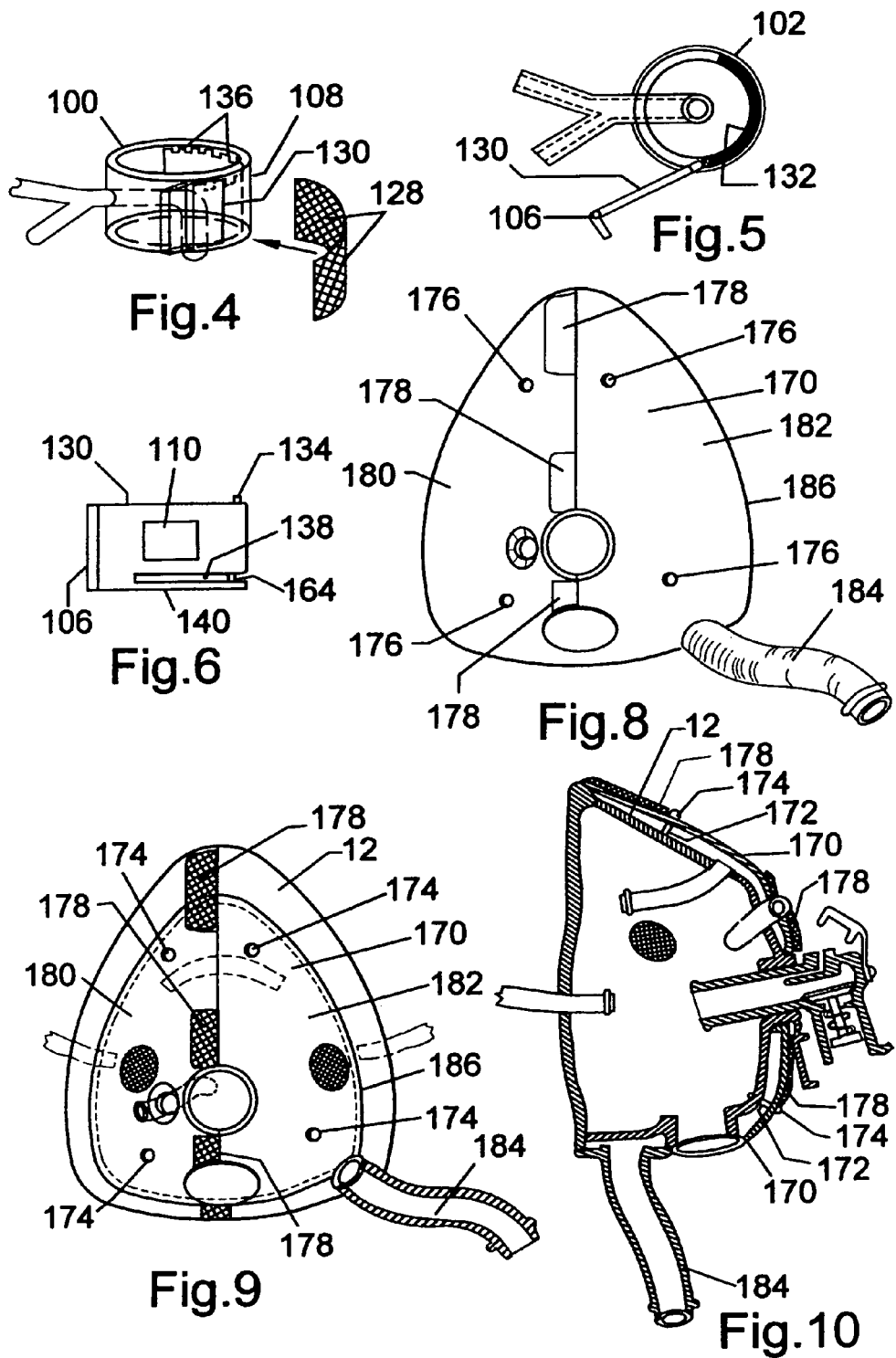

MULTITASK MEDICAL TREATMENT RESPIRATORY APPARATUS

This application is a continuation-in-part of U.S. patent application Ser. No. 10/439,612 filed May 15, 2003, now abandoned.

BACKGROUND OF THE INVENTION

This invention relates to apparatus for use in multitask medical treatment of the respiratory and other physiological organ systems of a patient. The new apparatus relates to the use of a mask having provision for retaining a medicant device with the mask for treatment with metered dose, nebulizer and other medication devices. A venturi device and reservoir bag for breathing may be included.

Various equipment exists for treatment of patients that have respiratory problems. There are some existing apparatus that may use a combination of a mask for the patient's face that may have provision for a reservoir bag with oxygen supply and simultaneous use of a nebulizer. The nebulizer may provide medicant directly into the mask or through the reservoir bag to the patient. For other medication treatment, such as, metered dose container devices, the mask may have to be removed to allow application using an alternate device. A device for solving the problem of multitask treatment of a patient, including provision for direct application of medicant to the patients mouth and thereby to the lungs while the mask may still be retained on the patient for breathing, does not appear to have been solved.

SUMMARY OF THE INVENTION

The present invention is directed to apparatus for multitask medical treatment of the respiratory system of a patient. The apparatus may have a mask defining a chamber wherein the mask may have a first port, a second port and a venting valve. A reservoir bag having a first opening may be in communication with the first port or there may be a venturi device intermediate the reservoir bag and the first port. In the alternative the venturi device may be in communication with a second opening of the reservoir bag. A gas source may be in communication with the venturi device. A medicant device intermediate the reservoir bag and the first port. In the alternative the venturi device may be mounted in the second port wherein the medicant device having a mouthpiece that may be inserted and retracted relative to the mask chamber and a patients mouth. The medicant device having a medicant chamber formed therein.

These and other features, aspects and advantages of the present invention will become better understood with reference to the following drawings, description and claims.

BRIEF DESCRIPTION OF THE DRAWINGS

FIG. 3 illustrates a front elevation partial cross section view of the multitask medical treatment respiratory apparatus according to an embodiment of the invention;

FIG. 3A illustrates a side cross section view of a cover cap;

FIG. 4 illustrates a perspective view of a venturi device according to an embodiment of the invention;

FIG. 5 illustrates a top plan view of a venturi device according to an embodiment of the invention;

FIG. 6 illustrates a side elevation view of an inner panel according to an embodiment of the invention;

FIG. 8 illustrates a front elevation view of the environmental control cover according to an embodiment of the invention;

FIG. 9 illustrates a front elevation view of the mask with anti-infection filters and environmental control cover according to an embodiment of the invention;

FIG. 10 illustrates a side elevation partial cross section view of the mask with anti-infection filters and environmental control cover according to an embodiment of the invention.

DETAILED DESCRIPTION

The following detailed description represents the best currently contemplated modes for carrying out the invention. The description is not to be taken in a limiting sense, but is made merely for the purpose of illustrating the general principles of the invention.

Figures 1, 1A:
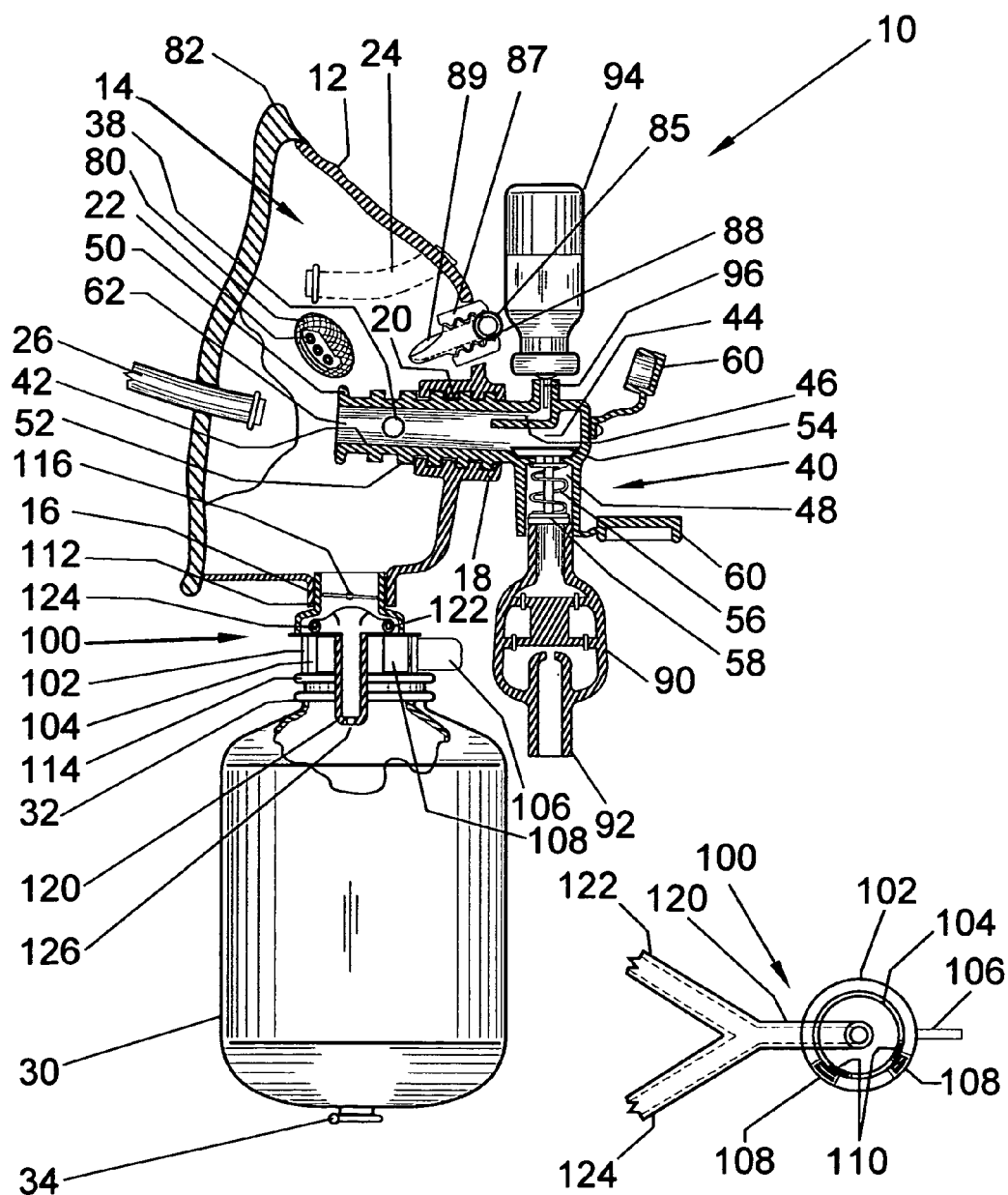
FIG. 1 illustrates a side elevation partial cross section view of the multitask medical treatment respiratory apparatus according to an embodiment of the invention.
FIG. 1A illustrates a bottom partial cross section view of a venturi apparatus according to an embodiment of the invention.

Referring to FIGS. 1 and 1A, a multitask medical treatment respiratory apparatus 10 may include a mask 12 defining a chamber 14 that may have a first port 16 for receipt of a first opening 32 of a reservoir bag 30. There may be a venturi device 100 intermediate the first port 16 and the first opening 32. The mask 12 may have a second port 18 for receipt of a mouthpiece 42 of a medicant device 40. There may also be a venting valve 22 that is a one-way valve to allow exhausting of gasses such as exhalant from the patient from the chamber 14. The mask 12 may have a pliant band 24 for shaping the mask 12 relative to a patients nose and an elastic strap 26 attached to retain the mask 12 on a patients head to cover the area around the mouth and nose.

Figures 2, 2A:
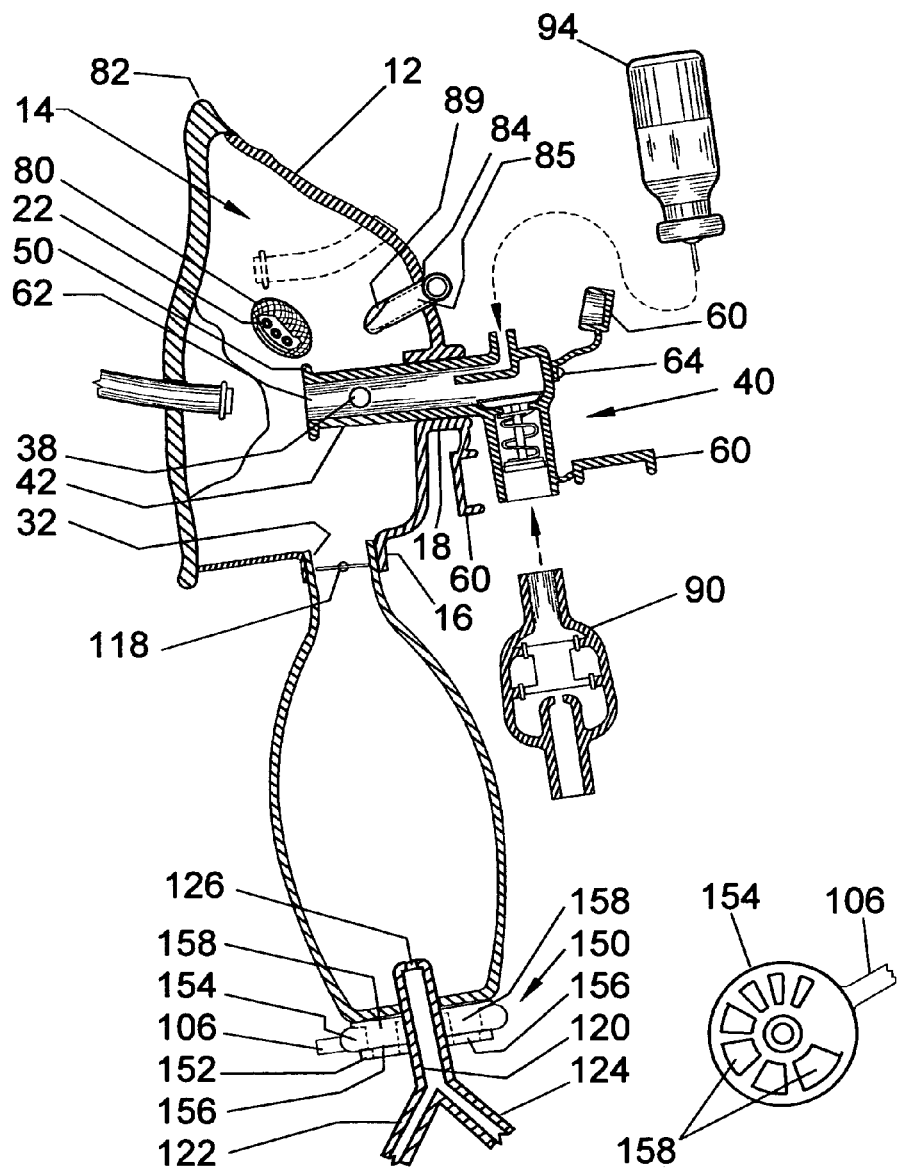
FIG. 2 illustrates a side elevation partial cross section view of the multitask medical treatment respiratory apparatus according to an embodiment of the invention.
FIG. 2A illustrates a top plan view of a disk according to an embodiment of the invention.
Figure 7:
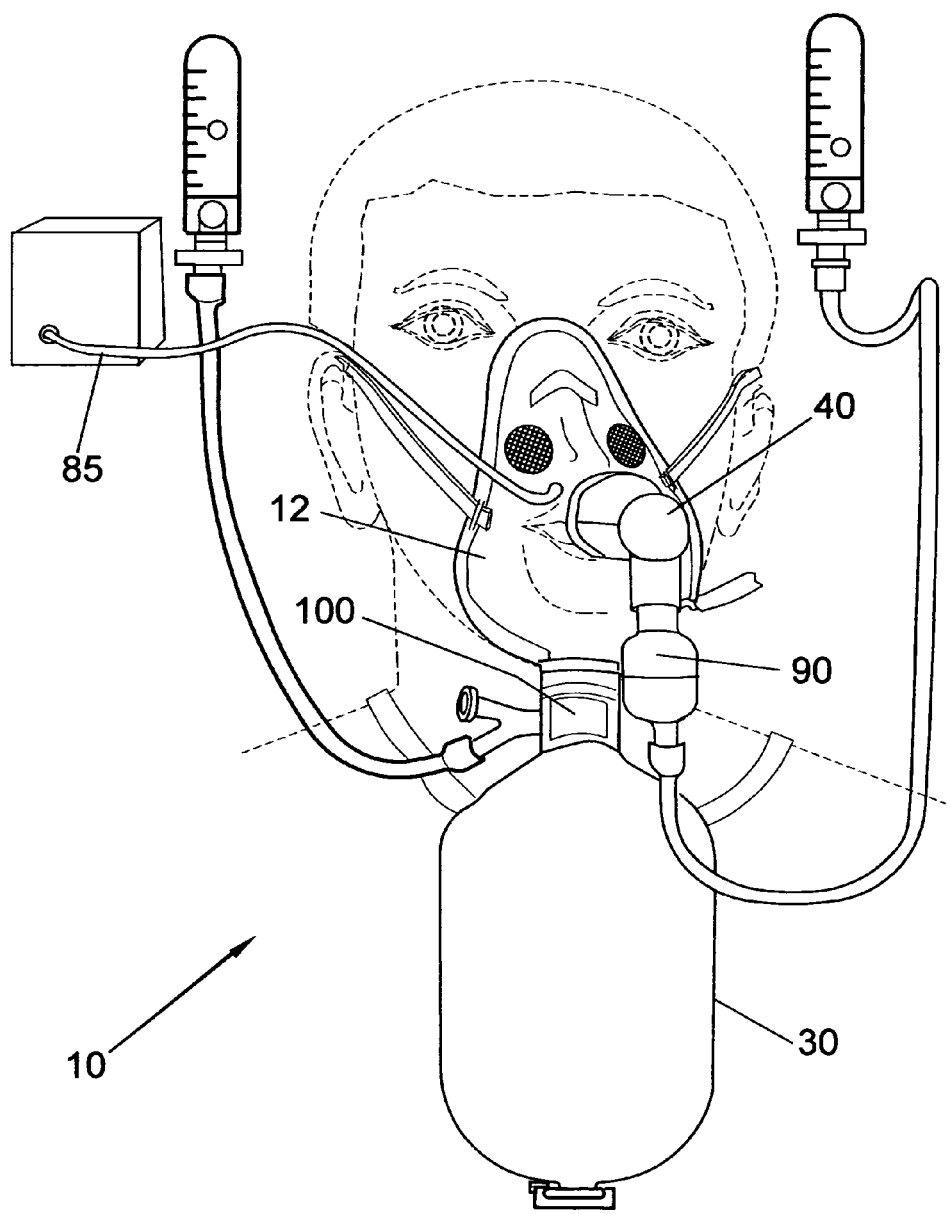
FIG. 7 illustrates a perspective view of the multitask medical treatment respiratory apparatus worn by a patient according to an embodiment of the invention.

The medicant device 40 may have a mouthpiece 42 and medicant chamber 44 that may include a metered passageway 46 and a nebulizer passageway 48. There may be one or more gas openings 38 in medicant device 40 located to allow gas in chamber 14 to be inhaled by the patient during various types of breathing treatments. The medicant device 40 may be retained in the second port 18 by frictional fit of the mouthpiece 42 and by use of a lip 50 at a chamber end 62. Alternatively the mouthpiece 42 and second port 18 may be threaded having cooperative threads 52 and 20 respectively. With the medicant device 40 mounted in the second port 18 the device may be readily available for medicant treatments by moving the mouthpiece 42 inwardly in chamber 14 such that a patient may engage their mouth with the mouthpiece 42 to directly receive medication and inhale gas through gas openings 38. This may be accomplished without removing the mask 12 or interrupting applications of other gasses or treatments introduced through first port 16 that may be inhaled through the nose. When the medicant device 40 is not being used, the device may be moved outwardly by pulling or rotating, in the case of a threaded device, to clear the area around the patient's mouth. The medicant device 40 may also be removed and stored when not needed and the second port 18 closed with a cover 60, as illustrated in FIG. 2.

The medicant device 40 may have a stem valve 54 with a spring 56 and a retainer tab 58 in the nebulizer passageway 48. The stem valve 54 may serve to open and close the nebulizer passageway 48 depending on whether or not a nebulizer 90 may be inserted therein. When a nebulizer 90 may be inserted opening stem valve 54, an oxygen or other gas source may be attached to nebulizer input 92 to cause the flow of nebulized medicant into medicant chamber 44.

A container 94 for application of a metered dose of medicant may have its output tube 96 inserted into metered passageway 46 for the introduction of the medicant into the medicant chamber 44. Covers 60 may be used to close the metered passageway 46 and nebulizer passageway 48 when they are not in use.

The venturi device 100 may have an outer wall 102 cylindrical element and an inner panel 104 element that may be in the form of a collar. The outer wall 102 may be attached to an upper channel 112 that may be inserted in first port 16 of mask 12 and may be retained by a metal band or like device. There may be a venturi valve 116 as a one-way valve to inhibit flow of gasses from mask 12 into the venturi device 100 and to serve as a back pressure valve to assist in maintaining inflation of reservoir bag 30. The outer wall 102 may be attached at its lower end 114 to the first opening 32 of the reservoir bag 30 in a similar manner. The inner panel 104 may be slidably engaged with the outer wall 102 and may be controlled for positioning by a tab 106. The outer wall 102 may have wall openings 108 and the inner panel 104 may have panel openings 110. Depending on the position of the inner panel 104 relative to the outer wall 102 the openings 108, 110 may control the amount of environmental air that may be drawn into reservoir bag 30.

There may be a venturi inlet tube 120 with nozzle 126 mounted in venturi device 100. There may be one or more inlet tubes as for example a first inlet tube 122 and a second inlet tube 124 connected to the venturi inlet tube 120. Also, two separate tubes 122, 124 could be mounted in the venturi device 100, each with its own terminating nozzle 126. Various inlet tubes 122, 124 may be used to introduce pure oxygen, combinations of oxygen and medicant, or other gasses. The flow of gas such as oxygen into the venturi device 100 through the venturi nozzle 126 may entrain environmental air if openings 108, 110 are in position to allow entry. The setting of the venturi device 100 and the introduction of gasses may allow for pure oxygen introduction into reservoir bag 30 as well as various other gas and medicant combinations. The reservoir bag 30 may have a second opening 34. It may be used as a drain port for accumulated moisture as well as other purposes.

Referring to FIGS. 2 and 2A, in another embodiment the multitask medical treatment respiratory apparatus 10 may be used with a rebreather configured reservoir bag 30. In this case the venturi device 150 may be inserted in the second opening 34 of the reservoir bag 30. The first opening 32 may be directly attached to the first port 16 of the mask 12. There may be a back pressure valve 118 in first opening 32 to assist in maintaining inflation of reservoir bag 30. The venturi device 150 may have an enclosure 152 with a rotatable disk 154 mounted therein. The venturi inlet tube 120 may be mounted in the center of enclosure 152 to protrude into the reservoir bag 30. The enclosure 152 may have enclosure openings 156 and the disk 154 may have disk opening 158. By rotating the disk 154 in the enclosure 152 the openings 156, 158 may be allowed to overlap or not. Depending on the overlap, the amount of environmental air entrained into the reservoir bag 30 may be controlled. One or a plurality of openings 156, 158 may be used as well as various sizes of openings.

FIG. 2 also illustrates a non-threaded second port 18 of the mask 12 and a non-threaded mouthpiece 42 of the medicant device 40. The mouthpiece 42 has been pushed into the chamber 14 for engagement by a patient using their mouth. When not necessary for such use the medicant device 40 may be pulled outwardly to be stopped by lip 50 in the stowed or nonuse position. The medicant device 40 may also be removed and stored when not needed and the second port 18 may be closed with a cover 60. The covers 60 may be removably attached by a cover tab 64. Other functional elements of the medicant device 40 may be as discussed previously.

Referring to FIGS. 3 and 3A, another embodiment of the multitask medical treatment respiratory apparatus 10 may include a mask 12 that uses the second port 18 for simple connection of a nebulizer 90 or a tubular medicant device 70. The tubular medicant device 70 may have gas inlet channel 72 for the patient to inhale medicant during treatment. A nebulizer 90 may be attached to the tubular medicant device 70 with nebulizer adapter 78. When the nebulizer 90 is not being used, it may be removed and a cover cap 76 may be used to cover the gas inlet channels 72. The gas openings 38 may serve the same function as previously discussed.

The chamber end 62 may be flexible for ease of closure of a users mouth on the tubular medicant device 70 or the chamber end 62 may have a generally oval shape. There may be one or more tubular protrusions 36 on the outside of tubular medicant device 70 for engagement with a second port groove 28 to aid in retaining the tubular medicant device 70 in mask 12.

There may be a metered passageway 74 formed in the side of the tubular medicant device 70 for introduction of metered dosages of medicant. A cover 60 may be provided to close the metered passageway 70 when not in use.

FIG. 3 illustrates an alternate venturi device 160 wherein the venturi inlet tube 120 terminates within the venturi device 160 below an inlet channel 162 that may be used to introduce gasses and/or medicant to be entrained and drawn into reservoir bag 30. The other features of the venturi device 160 may be similar to those discussed above with regard to the entrainment of environmental air. There may be a back pressure valve 118 in first opening 32 to assist in maintaining inflation of reservoir bag 30.

There may be a venturi outlet tube 121 connected to the venturi inlet tube 120 for connection of a pressure regulator 190 to regulate flow of a source gas, for example, oxygen introduced into venturi inlet tube 120, that may be input to the nebulizer 90 at the nebulizer input 92. Connecting tubing 204 may be used to connect a regulator inlet port 192 to the venturi outlet tube 121 and to connect a regulator outlet port 194 to the nebulizer input 92.

The pressure regulator 190 may have a regulator body 196 with an interior regulator cavity 198. A mesh material 200 may be contained in the regulator cavity 198 to smooth out gas flowing to the nebulizer 90. There may be a regulator adjustment valve 202 operable in the regulator inlet port 192 for positioning variably between an open and a closed position to allow increase or decrease of flow of the source gas to enter the nebulizer 90 for patient proper treatment.

Referring to FIGS. 4 through 6, an alternate inner panel 130 is illustrated for venturi device 100. The venturi device 100 may have outer wall 102 and an inner wall 132. An inner panel 130 may be made flexible to be slidably inserted between the outer wall 102 and inner wall 132. The outer wall 102 and inner wall 132 may have wall openings 108 as previously discussed to allow entry of environmental air. A venturi opening filter 128 for anti-infection/air filtration may be fitted over wall opening 108 to filter potential contaminants from entering the venturi device 100. The inner panel 130 may be moved to control the size of wall openings 108. The inner panel 130 may be of solid material or may have panel openings 110. The inner panel 130 may be provided with a protrusion 134 for engagement with one or more detents 136 formed in the outer wall 102. The inner panel 130 may have a slot opening 138 to form a fork element 140 that may be resilient. When a force is exerted to move the inner panel 130 in the venturi device 100, the fork element 140 may bend to allow disengagement of the protrusion 134 from a detent 136 thereby allowing movement of the inner panel 130 to a different detent position. A locking device 164 may be used to prevent the movement of the inner panel 130 once it has been placed in the proper detent 136 position.

Referring to FIGS. 1 through 3 and 7, anti-infectious filter material that may be biocompatible and capable of acting as a shield may be positioned on the mask 12 at venting valves 22 and at the mask edge 13. An anti-infection filter 80 may cover the venting valves 22 and an anti-infection border filter 82 may be attached to the mask edge 13 to inhibit the spread of a patient's infectious substances in a patient's exhaled breath.

A monitor port 84 may be formed in mask 12 to allow insertion of a monitor tube 85 that may be connected to an exhaled gas monitor device, for example to a CO 2 monitor device 86, to sample and measure a patient's exhaled pulmonary carbon dioxide or other exhaled gases. The monitor port 84 may have an adjustable element 87 such as threads 88 or ribs to engage corresponding elements on a monitor tube 85. This may allow positioning of the monitor tube 85 in the monitor port 84. The monitor tube inlet 89 may be a tube opening having an oval shape that may be positioned near a patient's nasal passage for receipt of exhaled gases from the patient.

Referring to FIGS. 8 through 10, an environmental control cover 170 may be positioned on the mask 12 to cover a portion of the outer surface of the mask 12. The environmental control cover 170 may have openings corresponding to the various ports and openings in the multitask medical treatment respiratory apparatus 10. The environmental control cover 170 may be positioned on the mask 12 on posts 172 attached to the mask 12. The posts 172 may have spherical ends 174 or other push attachment elements that may receive attachment openings 176 formed in the environmental control cover 170. Hook and loop devices 178 or other fasteners may also be used to retain the environmental control cover 170 on the mask 12. The environmental control cover 170 may also be formed of a right portion 180 and left portion 182 to aid in placing the environmental control cover 170 on the mask 12. The portions 180, 182 may be joined and attached by hook and loop devices 178 or other fasteners.

The environmental control mask may have an air tube 184 for connection to an air conditioning system (not shown) that may provide cooling or warming air to the interior of the environmental control mask 170 to circulate over the outer surface of the mask 12. The supplied air may be humidified and may escape at the control mask edge 186.

While the invention has been particularly shown and described with respect to the illustrated embodiments thereof, it will be understood by those skilled in the art that the foregoing and other changes in form and details may be made therein without departing from the spirit and scope of the invention.

Multitask Medical Treatment Respiratory Apparatus
CALL OUT LIST
FOR DRAWING ELEMENTS

| | |
|---|---|
| 10 | multitask medical treatment respiratory apparatus |
| 12 | mask |
| 13 | mask edge |
| 14 | chamber |
| 16 | first port |
| 18 | second port |
| 20 | threads |
| 22 | venting valve |
| 24 | pliant band |
| 26 | elastic strap |
| 28 | second port groove |
| 30 | reservoir bag |
| 32 | first opening |
| 34 | second opening |
| 36 | tubular protrusions |
| 38 | gas openings |
| 40 | medicant device |
| 42 | mouthpiece |
| 44 | medicant chamber |
| 46 | metered passageway |
| 48 | nebulizer passageway |
| 50 | lip |
| 52 | threads |
| 54 | stem valve |
| 56 | spring |
| 58 | retainer tab |
| 60 | covers |
| 62 | chamber end |
| 64 | cover tab |
| 70 | tubular medicant device |
| 72 | gas inlet channel |
| 74 | metered passageway |
| 76 | cover cap |
| 78 | nebulizer adapter |
| 80 | anti-infection filter |
| 82 | anti-infection border element |
| 84 | monitor port |
| 85 | monitor tube |
| 86 | CO2 monitor device |
| 87 | adjustable element |
| 88 | threads |
| 89 | monitor tube inlet |
| 90 | nebulizer |
| 92 | nebulizer input |
| 94 | container |
| 96 | output tube |
| 100 | venturi device |
| 102 | outer wall |
| 104 | inner panel |
| 106 | tab |
| 108 | wall opening |
| 110 | panel opening |
| 112 | upper channel |
| 114 | lower end |
| 116 | venturi valve |
| 118 | back pressure valve |
| 120 | venturi inlet tube |
| 121 | venturi outlet tube |
| 122 | first inlet tube |
| 124 | second inlet tube |
| 126 | nozzle |
| 128 | venturi opening filter |
| 130 | inner panel |
| 132 | inner wall |
| 134 | protrusion |
| 136 | detent |
| 138 | slot opening |
| 140 | fork element |
| 150 | venturi device |
| 152 | enclosure |
| 154 | disk |
| 156 | enclosure opening |
| 158 | disk opening |
| 160 | venturi device |
| 162 | inlet channel |
| 164 | locking device |
| 170 | environmental control cover |
| 172 | posts |
| 174 | spherical ends |
| 176 | attachment openings |

-continued

Multitask Medical Treatment Respiratory Apparatus
CALL OUT LIST
FOR DRAWING ELEMENTS

| | |
|---|---|
| 178 | hook and loop device |
| 180 | right portion |
| 182 | left portion |
| 184 | air tube |
| 186 | control mask edge |
| 190 | pressure regulator |
| 192 | regulator inlet port |
| 194 | regulator outlet port |
| 196 | regulator body |
| 198 | regulator cavity |
| 200 | mesh material |
| 202 | regulator adjustment valve |
| 204 | connecting tubing |

We claim:

1. An apparatus for multitask medical treatment of the respiratory system of a patient comprising:
    a mask defining a chamber wherein said mask having a first port, a second port and a venting valve;
    a reservoir bag having a first opening in communication with said first port and a back pressure valve mounted in said first opening;
    a variable control venturi device comprising:
    an enclosure with a disk rotatably mounted therein;
    said enclosure having an enclosure opening formed therein and said disk having a disk opening therein; and
    a venturi inlet tube protruding through said enclosure into said reservoir bag with a source of gas in communication with said venturi inlet tube;
    in communication with a second opening of said reservoir bag and a gas source in communication with said venturi device;
    a medicant device mounted in said second port wherein said medicant device having a mouthpiece that can be inserted and retracted in said chamber relative to a patient's mouth while said mask is positioned on a patient; and
    said medicant device having a medicant chamber formed therein and a gas opening formed therein.

2. The apparatus as in claim 1 wherein said medicant device having a metered passageway and a nebulizer passageway in communication with said medicant chamber.

3. The device as in claim 2 wherein said nebulizer passageway having a stem value mounted therein and biased in a closed position by a spring having a retainer tab.

4. The device as in claim 2 wherein said metered passageway having a cover and said nebulizer passageway having a cover.

5. The apparatus as in claim 1 wherein said mouthpiece having a lip at a chamber end.

6. The apparatus as in claim 1 wherein said mouthpiece having threads for threadable engagement with said second port having threads therein.

7. The apparatus as in claim 1 wherein an anti-infection filter is disposed on said venting valve spaced apart from said venting valve for proper function of said venting valve; and said anti-infection filter is impregnated with an anti-infection chemical to inhibit the spread of human infectious substances in a patient's exhaled breath.

8. The apparatus as in claim 1 wherein an anti-infection border element is disposed on a mask edge of said mask and said anti-infection border element is impregnated with an anti-infection chemical to inhibit the spread of human infectious substances in a patient's exhaled breath.

9. The apparatus as in claim 1 wherein said mask having a monitor port adjacent said second port and a monitor tube disposed in said monitor port connectable to an exhaled gas monitor device.

10. The apparatus as in claim 9 wherein said monitor port having an adjustable element.

11. The apparatus as in claim 1 wherein there is an environmental control cover disposed on said mask and attached thereto.

12. The apparatus as in claim 11 wherein said mask having a plurality of posts with attachment ends and said environmental control cover having a plurality of attachment openings therein positioned to be received on said plurality of posts.

13. The apparatus as in claim 11 wherein said environmental control cover is retained to said mask by a plurality of hook and loop devices.

14. The apparatus as in claim 11 wherein said environmental control cover having an air tube connectable to an air conditioning system.

15. The apparatus as in claim 11 wherein said environmental control mask comprising a right portion and a left portion attached by a plurality of hook and loop devices.

16. An apparatus for multitask medical treatment of the respiratory system of a patient comprising:
    a mask defining a chamber wherein said mask having a first port, a second port and a venting valve;
    a reservoir bag having a first opening in communication with said first port and a back pressure valve mounted in said first opening;
    a variable control venturi device comprising;
    an outer wall and an inner panel movable relative to said outer wall;
    an upper channel of said venturi device in communication with said first port and with an inlet channel;
    a venturi inlet tube mounted in said venturi device below said upper channel; and
    said outer wall having a wall opening;
    in communication with a second opening of said reservoir bag and a gas source in communication with said venturi device;
    a medicant device mounted in said second port wherein said medicant device having a mouthpiece that can be inserted and retracted in said chamber relative to a patient's mouth while said mask is positioned on a patient; and
    said medicant device having a medicant chamber formed therein and a gas opening formed therein.

17. The apparatus as in claim 16 wherein said medicant device having a metered passageway and a nebulizer passageway in communication with said medicant chamber.

18. The device as in claim 17 wherein said nebulizer passageway having a stem value mounted therein and biased in a closed position by a spring having a retainer tab.

19. The device as in claim 17 wherein said metered passageway having a cover and said nebulizer passageway having a cover.

20. The apparatus as in claim 16 wherein said mouthpiece having a lip at a chamber end.

21. The apparatus as in claim 16 wherein said mouthpiece having threads for threadable engagement with said second port having threads therein.

22. The apparatus as in claim 16 wherein an anti-infection filter is disposed on said venting valve spaced apart from said venting valve for proper function of said venting valve; and said anti-infection filter is impregnated with an anti-infection chemical to inhibit the spread of human infectious substances in a patient's exhaled breath.

23. The apparatus as in claim 16 wherein an anti-infection border element is disposed on a mask edge of said mask and said anti-infection border element is impregnated with an anti-infection chemical to inhibit the spread of human infectious substances in a patient's exhaled breath.

24. The apparatus as in claim 16 wherein said mask having a monitor port adjacent said second port and a monitor tube disposed in said monitor port connectable to an exhaled gas monitor device.

25. The apparatus as in claim 24 wherein said monitor port having an adjustable element.

26. The apparatus as in claim 16 wherein there is an environmental control cover disposed on said mask and attached thereto.

27. The apparatus as in claim 26 wherein said mask having a plurality of posts with attachment ends and said environmental control cover having a plurality of attachment openings therein positioned to be received on said plurality of posts.

28. The apparatus as in claim 26 wherein said environmental control cover is retained to said mask by a plurality of hook and loop devices.

29. The apparatus as in claim 26 wherein said environmental control cover having an air tube connectable to an air conditioning system.

30. The apparatus as in claim 26 wherein said environmental control mask comprising a right portion and a left portion attached by a plurality of hook and loop devices.

31. An apparatus for multitask medical treatment of the respiratory system of a patient comprising:
   a mask defining a chamber wherein said mask having a first port, a second port and a venting valve;
   a variable control venturi device comprising:
   an outer wall and an inner panel movable relative to said outer wall;
   an upper channel inserted in said first port and having a venturi valve therein;
   a lower end inserted in said first opening;
   a venturi inlet tube having a nozzle mounted in said venturi device with said nozzle oriented downwardly toward said reservoir bag; and
   said outer wall having a wall opening;
   in communication with said first port and a reservoir bag having a first opening in communication with said venturi device;
   a gas source in communication with said venturi device;
   a medicant device mounted in said second port wherein said medicant device having a mouthpiece that may be inserted and retracted in said chamber relative to a patient's mouth while said mask is positioned on a patient; and
   said medicant device having a medicant chamber formed therein and a gas opening formed therein.

32. The apparatus as in claim 31 wherein said medicant device having a metered passageway and a nebulizer passageway in communication with said medicant chamber.

33. The device as in claim 32 wherein said nebulizer passageway having a stem value mounted therein and biased in a closed position by a spring having a retainer tab.

34. The device as in claim 32 wherein said metered passageway having a cover and said nebulizer passageway having a cover.

35. The apparatus as in claim 31 wherein said mouthpiece having a lip at a chamber end.

36. The apparatus as in claim 31 wherein said mouthpiece having threads for threadable engagement with said second port having threads therein.

37. The device as in claim 31 wherein said inner panel having a panel opening.

38. The device as in claim 31 wherein said inner panel having a tab.

39. The device as in claim 31 wherein said venturi inlet tube in communication with a first inlet tube and a second inlet tube.

40. The device as in claim 31 wherein said venturi device further comprising:
   an inner wall interior to said inner panel;
   said inner panel having a protrusion for engagement with said outer wall having a plurality of detents formed therein; and
   said inner panel having a slot opening defining a fork element.

41. The device as in claim 40 wherein a locking device inhibits movement of said inner panel.

42. The device as in claim 31 wherein said wall opening having a venture opening filter attached.

43. An apparatus for multitask medical treatment of the respiratory system of apatient comprising:
   a mask defining a chamber wherein said mask having a first port, a second port and a venting device;
   a reservoir bag having a first opening and a second opening wherein said first opening in communication with said first port and said second opening in communication with a variable control venturi device having a venturi inlet tube that has a venturi outlet tube;
   a pressure regulator having a regulator inlet port connectable to said venturi outlet tube and a regulator outlet port connectable to said nebulizer at a nebulizer input;
   said regulator having a regulator body having a cavity therein and a mesh material disposed in said cavity;
   a regulator adjustment valve operable in said regulator inlet port;
   a back pressure valve mounted in said first opening;
   a tubular medicant device insertable in said second port and having a gas inlet channel and a metering passageway; and
   said tubular medicant device having a gas opening formed therein.

44. The apparatus as in claim 43 wherein a nebulizer is attached to said tubular medicant device.

45. The apparatus as in claim 43 wherein said second port having a second port groove formed therein for engagement of a tubular protrusion of said tubular medicant device.

* * * * *